United States Patent [19]
Levitas et al.

[11] Patent Number: 6,053,887
[45] Date of Patent: *Apr. 25, 2000

[54] MEDICAL TREATMENT APPARATUS AND METHOD

[75] Inventors: Doron Levitas; Shan Padda, both of Chicago, Ill.; Alan E. Jordan, San Diego, Calif.; Sam Russo, Lisle, Ill.; Larry Wilson, Poway, Calif.

[73] Assignee: Baxter Healthcare Inc., Deerfield, Ill.

[ * ] Notice: This patent is subject to a terminal disclaimer.

[21] Appl. No.: 09/206,075

[22] Filed: Dec. 4, 1998

Related U.S. Application Data

[63] Continuation of application No. 08/703,543, Aug. 27, 1996, Pat. No. 5,895,371.

[51] Int. Cl.$^7$ .................................................. A61M 31/00
[52] U.S. Cl. ............................................. 604/49; 604/65
[58] Field of Search ................................. 604/65, 66, 67, 604/49, 50, 151, 152, 153, 154, 155

[56] References Cited

U.S. PATENT DOCUMENTS

| | | | |
|---|---|---|---|
| 3,739,943 | 6/1973 | Wilhelmson et al. | 222/59 |
| 3,858,574 | 1/1975 | Page | 128/205 T |
| 3,910,257 | 10/1975 | Fletcher et al. | 128/2.1 A |

(List continued on next page.)

OTHER PUBLICATIONS

A.H. McMorris, J.L. Kelleway, B. Tapadia and E. L. Dohmann, "Are Process Control Rooms Obsolete?", taken from Control Engineering, pp. 42–47, Jul., 1971.

Abbott Laboratories, The Blue Line System, Lifecare, copyright, 1990.

L.C. Sheppard, "Computer Based Clinical Systems: Automation and Integration," taken from 39th ACEMB, Sep. 13–16, 1986; pp. 73–75.

"Block Medical: Growing With Home Infusion Therapy," taken from INVIVO, The Business and Medicine Report, Apr., 1991; pp. 7–9.

"IEEE–488 and VXIbus Control, Data Acquisition, and Analysis... the Most Choices," select pages taken from National Instruments, Application Software Products and Application Software Overview, (1991) 17 pages.

"LabView®2 User Manual; Chapter 2, The Front Panel," taken from National Instruments Corporation, Jan., 1990; pp. 1–36.

J. C. Crone, Jaromir Belic and Roger W. Jelliffe, M.D., "A Programmable Infusion Pump Controller," taken from 30th Annual Conference on Engineering in Medicine and Biology, Nov. 5–9, 1977; pp. A–35827 through A–35837.

Selective portions of Chapter 9 of Mayhew, "Principles and Guidelines In Software User Interface Design," Prentice Hall PTR, Englewood Cliffs, New Jersey, 1992.

(List continued on next page.)

*Primary Examiner*—Michael Buiz
*Assistant Examiner*—Daphna Shai
*Attorney, Agent, or Firm*—Perry Hoffman

[57] ABSTRACT

A medical treatment apparatus is provided with a programmable medical device disposed at a first room location and a remote monitor and/or controller disposed at a second room location. The programmable medical device is used to administer a medical treatment to a patient, and the remote monitor/controller maybe used to monitor the operation of the medical device, control the operation of the medical device, and/or to transfer data from the medical device to the remote monitor/controller. The apparatus may allow voice communication between the remote monitor/controller and the patient who is receiving treatment via the medical device while the medical device is being monitored and/or controlled from the remote location. The remote monitor/controller may also include means for determining the type of medical device to which it is connected. The programmable medical device includes various types of sensors for generating patient medical condition data which is transmitted to the remote monitor/controller. The medical treatment provided to the patient can be changed in response to analysis of the patient medical data at the remote location.

15 Claims, 13 Drawing Sheets

U.S. PATENT DOCUMENTS

| | | | |
|---|---|---|---|
| 4,173,971 | 11/1979 | Karz | 128/702 |
| 4,413,314 | 11/1983 | Slater et al. | 364/188 |
| 4,449,538 | 5/1984 | Corbitt et al. | 128/760 |
| 4,531,527 | 7/1985 | Reinhold, Jr. et al. | 128/696 |
| 4,561,443 | 12/1985 | Hogrefe et al. | 128/419 PG |
| 4,586,260 | 5/1986 | Baxter et al. | 33/125 C |
| 4,624,661 | 11/1986 | Arimond | 604/151 |
| 4,676,776 | 6/1987 | Howson | 604/31 |
| 4,696,671 | 9/1987 | Epstein et al. | 604/67 |
| 4,731,051 | 3/1988 | Fischell | 606/67 |
| 4,756,706 | 7/1988 | Kerns et al. | 604/66 |
| 4,797,840 | 1/1989 | Fraden | 364/557 |
| 4,803,625 | 2/1989 | Fu et al. | 364/413.03 |
| 4,810,243 | 3/1989 | Howson | 604/31 |
| 4,828,545 | 5/1989 | Epstein et al. | 604/66 |
| 4,850,972 | 7/1989 | Schulman et al. | 604/151 |
| 4,865,584 | 9/1989 | Epstein et al. | 604/67 |
| 4,901,221 | 2/1990 | Kodosky et al. | 364/200 |
| 4,925,444 | 5/1990 | Orkin et al. | 604/80 |
| 4,933,843 | 6/1990 | Scheller et al. | 364/413.01 |
| 4,942,514 | 7/1990 | Miyagaki et al. | 364/190 |
| 4,952,928 | 8/1990 | Carroll et al. | 340/825.54 |
| 4,995,268 | 2/1991 | Ash et al. | 73/861.05 |
| 5,038,800 | 8/1991 | Oba | 128/904 |
| 5,078,683 | 1/1992 | Sancoff et al. | 604/67 |
| 5,100,380 | 3/1992 | Epstein et al. | 604/67 |
| 5,109,849 | 5/1992 | Goodman et al. | 128/633 |
| 5,115,133 | 5/1992 | Knudon | 250/341 |
| 5,116,312 | 5/1992 | Blankenship et al. | 604/66 |
| 5,137,023 | 8/1992 | Mendelson et al. | 128/633 |
| 5,152,296 | 10/1992 | Simons | 128/670 |
| 5,153,827 | 10/1992 | Coutré et al. | 364/413.02 |
| 5,155,693 | 10/1992 | Altmayer et al. | 364/550 |
| 5,165,874 | 11/1992 | Sancoff et al. | 417/474 |
| 5,167,235 | 12/1992 | Seacord et al. | 128/664 |
| 5,191,891 | 3/1993 | Righter | 128/710 |
| 5,207,642 | 5/1993 | Orkin et al. | 604/65 |
| 5,213,099 | 5/1993 | Tripp, Jr. | 128/633 |
| 5,226,425 | 7/1993 | Righter | 128/710 |
| 5,230,623 | 7/1993 | Guthrie et al. | 433/72 |
| 5,256,157 | 10/1993 | Samiotes et al. | 604/246 |
| 5,291,190 | 3/1994 | Scarola et al. | 340/825.06 |
| 5,295,062 | 3/1994 | Fukushima | 364/188 |
| 5,297,554 | 3/1994 | Glynn et al. | 128/665 |
| 5,317,506 | 5/1994 | Coutré et al. | 364/413.02 |
| 5,338,157 | 8/1994 | Blomquist | 417/2 |
| 5,361,758 | 11/1994 | Hall et al. | 128/633 |
| 5,368,562 | 11/1994 | Blomquist et al. | 604/65 |
| 5,376,070 | 12/1994 | Purvis et al. | 604/31 |
| 5,378,231 | 1/1995 | Johnson et al. | 604/67 |
| 5,395,321 | 3/1995 | Kawahara et al. | 604/67 |
| 5,395,329 | 3/1995 | Fleitschhackor et al. | 604/95 |
| 5,400,246 | 3/1995 | Wilson et al. | 364/146 |
| 5,412,400 | 5/1995 | Takahara et al. | 345/119 |
| 5,429,602 | 7/1995 | Hauser | 604/65 |
| 5,469,855 | 11/1995 | Pompei et al. | 128/664 |
| 5,482,446 | 1/1996 | Williamson et al. | 417/474 |
| 5,485,408 | 1/1996 | Blomquist | 364/578 |
| 5,509,422 | 4/1996 | Fukami | 128/670 |
| 5,522,396 | 6/1996 | Langer et al. | 128/696 |
| 5,544,651 | 8/1996 | Wilk | 128/633 |
| 5,555,638 | 9/1996 | Evers et al. | 604/66 |
| 5,573,506 | 11/1996 | Vasko | 604/65 |
| 5,582,593 | 12/1996 | Hultman | 604/65 |
| 5,643,212 | 7/1997 | Coutré et al. | 604/131 |

OTHER PUBLICATIONS

Electronic's Article of Feb., 1990, by Jack Shandle, entitled "Who Will Dominate the Desktop in the '90s," pp. 48–50.

Chapter 5 entitled "Direct Manipulation" from Shneiderman "Designing the User Interface: Strategies for Effective Human–Computer Interaction," Addison–Wesley Publishing Company, Second Edition, ©1992, reprinted with corrections 1993.

Literature of Baxter's MultiPlex™ Series 100 Fluid Management System, 2 pp., no date listed.

Literature of Baxter "Introducing MultiPlex™ Series 100 Fluid Management System," copyright 1988.

Literature describing Baxter's Flo–Gard®6201 Volumetric Infusion Pump, copyrighte 1992.

Literature of I–Flow Corporation advertising its Vivus 4000 Infusion System.

One–page article by Jerry Hirsch entitled "Portable IV Frees Patients," printed in The Orange County Register, D section, Nov. 21, 1991.

Bedder, et al., "Cost Analysis of Two Implantable Narcotic Delivery Systems," Journal of Pain And Symptom Management, vol. 6, No. 6, Aug., 1991, pp. 368–373.

Peter Lord, Hossein Allami, Mark Davis, Raul Dias, Patrice Heck, and Robert Fischell, pp. 66–71 from book chapter entitled "MiniMed Technologies Programmable Implantable Infusion System," describing clinical trials from Nov., 1986.

"IMED®Status™ Infusion Management System," 6 page brochure, IMED Corporation, San Diego, CA, no date listed.

James D. Foley and Andries Van Dam "Fundamentals of Interactive Computer Graphics," selected pages from Chapters 1 and 2, Addison–Wesley Publishing Company, ©1982, reprinted with corrections 1983.

Fig.15.

| PATIENT NAME: | PATIENT ID NUMBER: | BEGINNING DATE: | ENDING DATE: |
|---|---|---|---|
| | | | |

☐ MALFUNCTIONS AND ALARMS ☐ PUMP TURNED ON ☐ PIGGYBACKS
☐ THERAPIES PROGRAMMED ☐ PUMP TURNED OFF ☐ TITRATIONS AND RATECHANGES
☐ THERAPIES STARTED ☐ PUMP ON HOLD ☐ BOLUS STATUS
☐ THERAPIES COMPLETED ☐ PUMP RESTARTED ☐ PATIENT IDS
☐ THERAPIES RESUMED ☒ ALL DATA ☐ INFUSION DATA

| DISPLAY | PRINT | SAVE TO DISK | EXIT |

US 6,053,887

MEDICAL TREATMENT APPARATUS AND METHOD

This is a continuation, of prior application Ser. No. 08/703,543, filed Aug. 27, 1996 now U.S. Pat. No. 5,895,321 which is hereby incorporated herein by reference in its entirety.

BACKGROUND OF THE INVENTION

The present invention is directed to a medical treatment apparatus and method for automatically administering a medical treatment to a patient via a medical treatment device, such as an infusion pump, disposed at a first location and a monitoring and/or controlling device disposed at a remote location.

An infusion pump is used to automatically administer liquid medicant to a patient. The liquid medicant is supplied from a source of medicant and pumped into the patient via a catheter or other injection device. The manner in which the liquid is infused is controlled by the infusion pump, which may have various modes of infusion, such as a continuous mode in which the liquid medicant is continuously infused at a constant rate, or a ramp mode in which the rate of infusion gradually increases, then remains constant, and then gradually decreases.

Prior art systems have been described which monitor the medical condition of a patient at a patient location using a sensing apparatus which has various types of sensors, such as a sensor for generating heart rate data and a temperature sensor for monitoring the temperature in the ear canal of the patient. Such a prior art system included a remote monitoring device provided at a location remote from the sensing apparatus to which sensing data was transmitted, and the remote monitoring device transmitted control signals to the sensing apparatus at the patient location to control the operation of the sensing apparatus, such as by controlling the sampling rate of the sensors. Such a prior art system also included display means at the remote location for generating visual displays relating to the sensed medical conditions.

One example of such a prior art system is disclosed in U.S. Pat. No. 3,910,257 to Fletcher, et al. That patent discloses a sensing apparatus in the form of a bio-belt unit 11, 12 and a remote monitoring device in the form of a data acquisition unit 14. The bio-belt unit 11, 12 incorporates different types of sensors, including an ear canal sensor 21 and a plurality of ECG electrodes 22. The data acquisition unit 14 receives patient medical data from the bio-belt unit 11, 12 and also transmits control commands to control the operation of the bio-belt unit 11, 12. See e.g. FIG. 2; column 5, lines 1–7; column 6, lines 6–10; and column 6, lines 39–47 of the Fletcher, et al. patent.

U.S. Pat. No. 5,038,800 to Oba also discloses the concept of providing a patient monitoring apparatus at a patient location and a remote monitoring device having the capability of receiving patient medical data from the patient monitoring apparatus and controlling the operation of the patient monitoring apparatus from a remote location. The patient monitoring apparatus is provided as a number of bedside monitors 3A–3C, and the remote monitoring apparatus is provided is in the form of a central monitor 2. The Oba patent discloses that the bedside monitors 3A–3C and the central monitor 2 are interconnected via a local area network (LAN). The operation of the bedside monitors 3A–3C can be controlled from the central monitor 2. See, for example, column 4, lines 4–11; column 4, lines 24–27; and column 4, lines 40–42 of the Oba patent.

U.S. Pat. No. 4,803,625 to Fu, et al. also discloses the concept of providing a patient monitoring apparatus at a patient location and a remote monitoring device having the capability of receiving patient medical data from the patient monitoring apparatus. As shown in FIG. 2 of the Fu, et al. patent, the patient monitoring apparatus is provided in the form of a number of home units 60, each of which includes a number of sensors, including a blood pressure module 92, a scale module 84, a temperature module 86, and an ECG electrode unit 90. Each of the home units 60 is connected to a central unit 20 via a modem 62 connected to each home unit 60 and a modem 22 connected to the central unit 20. The Fu, et al. patent also generates medication reminders to a patient. See, for example, FIG. 13.

SUMMARY OF THE INVENTION

The invention is directed to a medical treatment apparatus having programmable medical treatment means for automatically administering a medical treatment directly to a patient, the programmable medical treatment means being disposed at a first room location, a sensor for detecting a medical condition of the patient, the sensor being disposed at the first room location and being connected to the patient, and a remote controller for controlling the programmable medical treatment means, the remote controller being disposed at a second room location remote from the first room location at which the programmable medical treatment means is disposed. The remote controller includes means for controlling the programmable medical treatment means to allow the medical treatment being administered to the patient to be changed, and the medical treatment apparatus also includes remote monitoring means operatively coupled to the sensor for monitoring the medical condition detected by the sensor, the remote monitoring means being disposed at the second room location.

The programmable medical treatment means may be an infusion pump for infusing a drug into the patient, the infusion pump being composed of a liquid injection device adapted to be connected to the patient, a conduit connected to the liquid injection device, a pumping mechanism for pumping a liquid drug through the conduit and into the patient via the liquid injection device, and a controller for controlling the pumping mechanism.

The invention is also directed to a method of administering a medical treatment to a patient via a programmable medical treatment apparatus. The method includes the steps of: (a) automatically administering a medical treatment to a patient with a programmable medical treatment apparatus disposed at a first room location, (b) detecting a medical condition of the patient with a sensor at the first room location, (c) transmitting medical condition data relating to the medical condition from the first room location to a second room location, and (d) transmitting a control command from the second room location to the programmable medical treatment apparatus at the first room location to change the medical treatment automatically administered during step (a), the control command being based upon the medical condition data transmitted during step (c).

The method may also include the step of analyzing the medical condition data prior to transmitting the control command, the step of displaying the medical condition data on a visual display disposed at the second room location, and the step of storing the medical condition data in the memory of a remote monitor/controller disposed at the second room location.

These and other features and advantages of the present invention will be apparent to those of ordinary skill in the art in view of the detailed description of the preferred embodiment, which is made with reference to the drawings, a brief description of which is provided below.

BRIEF DESCRIPTION OF THE DRAWINGS

FIG. 15 is an illustration of a graphical user menu that may be displayed by the remote monitor/controller.

DETAILED DESCRIPTION OF A PREFERRED EMBODIMENT

Figure 1:
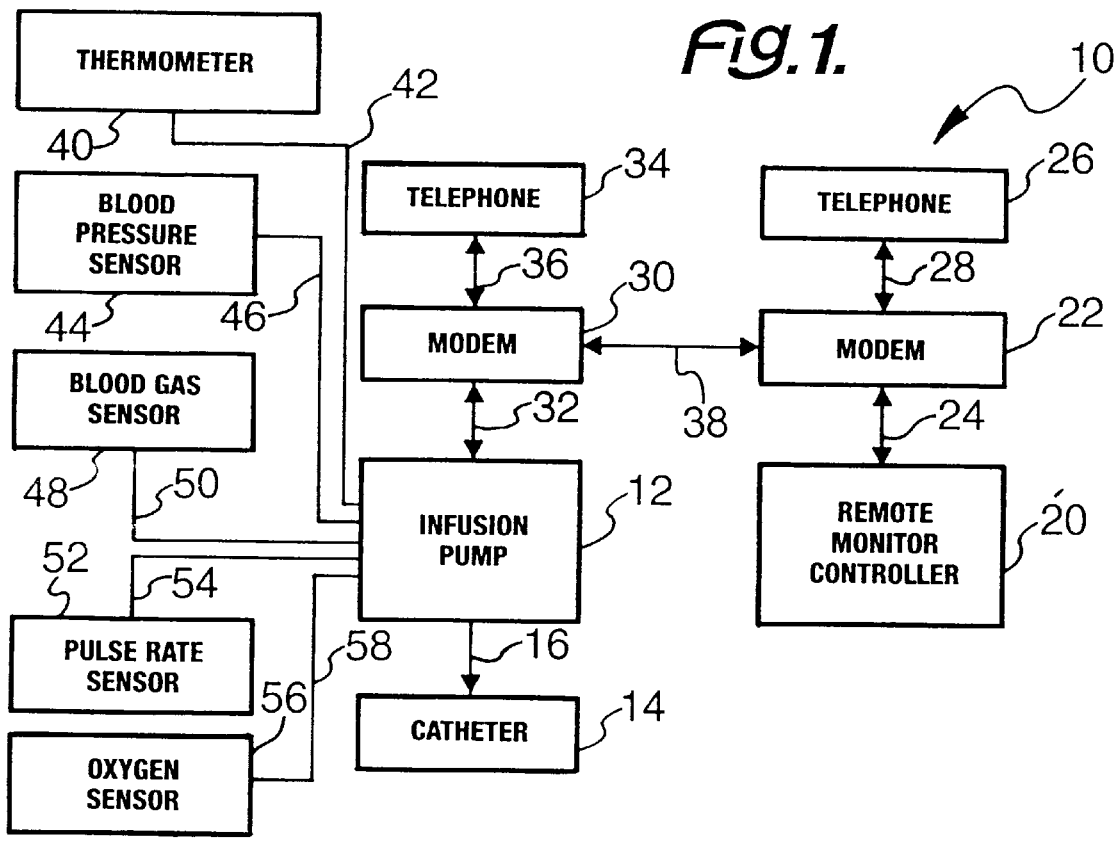
FIG. 1 is a block diagram of an apparatus for administering medical treatment to a patient and monitoring the condition of the patient.

FIG. 1 illustrates one embodiment of an apparatus 10 for administering medical treatment to a patient and monitoring the condition of the patient. Referring to FIG. 1, the apparatus 10 includes a programmable medical treatment means in the form of an infusion pump 12, which is connected to a liquid medicant injection device in the form of a catheter 14 via a liquid conduit schematically shown as 16.

The apparatus 10 includes a remote monitor/controller 20 which is disposed at a room location remote from the room location at which the infusion pump 12 is located. The remote monitor/controller 20 could be disposed in a different room of the same building in which the pump 12 is disposed, or in a different building than the one in which the pump 12 is disposed. The remote monitor/controller 20 is connected to a conventional voice/data modem 22 via a data link 24, and the modem 22 is also connected to a telephone 26 via a voice link 28. The infusion pump 12 is connected to a conventional voice/data modem 30 via a data link 32, and the modem 30 is connected to a telephone 34 via a voice link 36. The two modems 22, 30 are interconnected to bidirectional voice and data communication via a communication link 38, which could be a telephone line, for example.

The infusion pump 12 is connected to five conventional sensors which are connected to the patient and which detect various medical conditions of the patient. The sensors include a thermometer 40 connected to the infusion pump 12 via a line 42, a blood pressure sensor 44 connected to the pump 12 via a line 46, a blood gas sensor 48 connected to the pump 12 via a line 50, a pulse rate sensor 52 connected to the pump 12 via a line 54, and a blood-oxygen sensor 56 connected to the pump 12 via a line 58. Not all of the sensors 40, 44, 48, 52, 56 are required for operation of the apparatus 10, and other types of sensors could be used.

Figure 2:
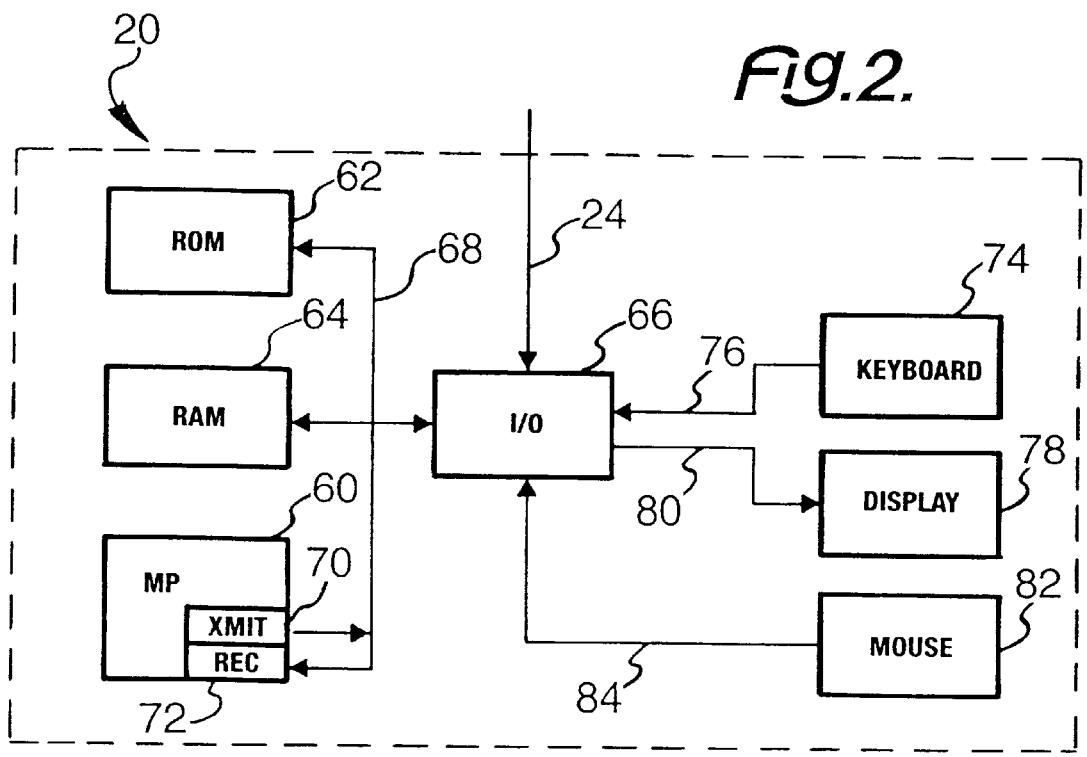
FIG. 2 is a block diagram of the electronic components of the remote monitor/controller shown schematically in FIG. 1.

FIG. 2 is a block diagram of the electronics of the remote monitor/controller 20 shown schematically in FIG. 1. Referring to FIG. 2, the remote monitor/controller 20 includes a microprocessor (MP) 60, a read-only memory (ROM) 62, a random-access memory (RAM) 64, and an input/output (I/O) circuit 66, all of which are interconnected by an address/data bus 68. The microprocessor 60 has a transmit buffer (XMIT) 70 for transmitting data bytes and a receive buffer (REC) 72 for receiving data bytes. The remote monitor/controller 20 has a keyboard 74 connected to the I/O circuit 66 via a line 76, a display device 78, such as a CRT, connected to the I/O circuit 66 via a line 80, and an input device, such as an electronic mouse 82, connected to the I/O circuit 66 via a line 84. The remote monitor/controller 20 can also include one or more disk drives, such as a hard disk drive or a floppy disk drive.

Figure 3:
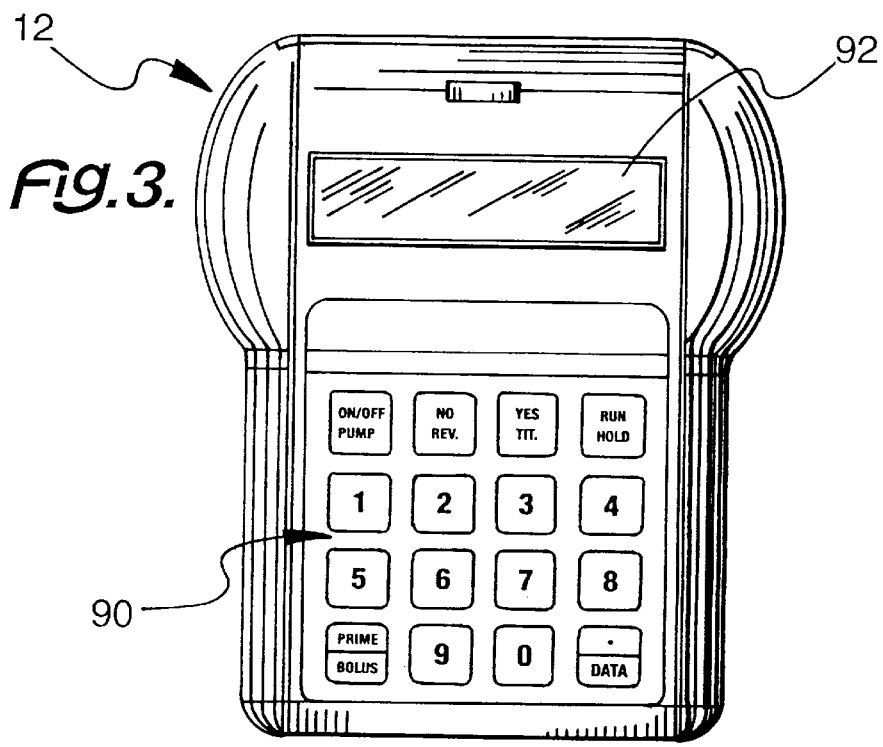
FIG. 3 is a front view of one embodiment of the infusion pump shown schematically in FIG. 1.

FIG. 3 is a front view of one embodiment of the infusion pump 12 shown schematically in FIG. 1. Referring to FIG. 3, the pump 12 has an input device in the form of a keypad 90 via which a user may input data and commands and a display 92 for displaying textual messages to the user.

Figure 4:
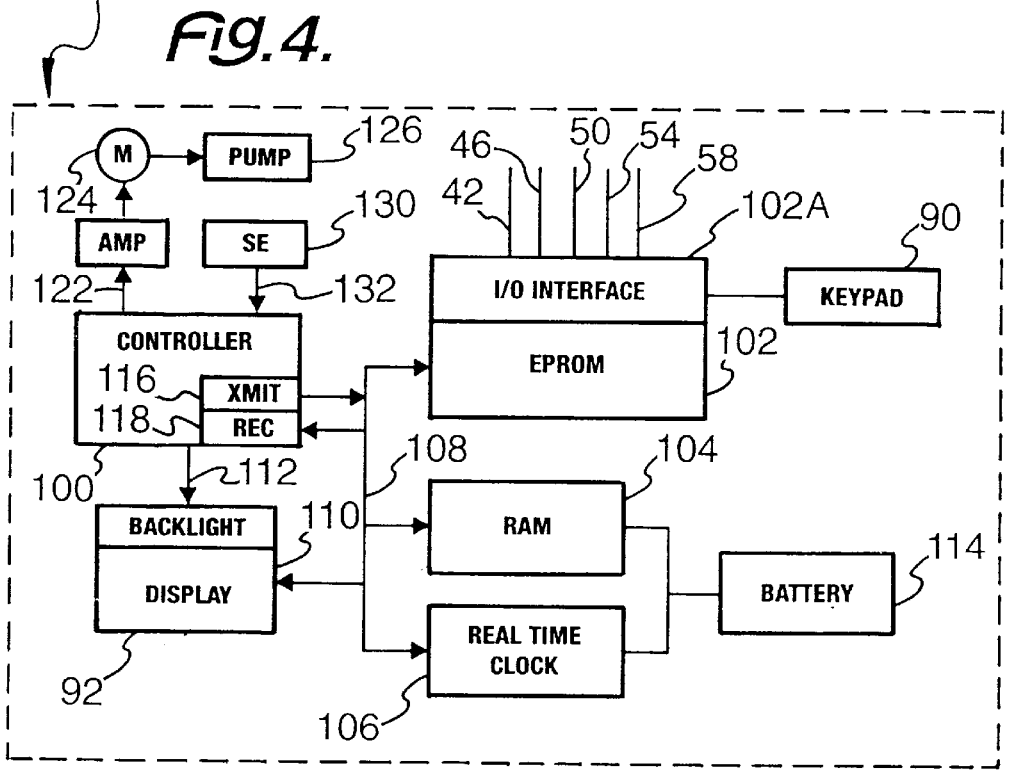
FIG. 4 is a block diagram of the electronic components of the infusion pump of FIG. 3.

A block diagram of the electronics of the infusion pump 12 is shown in FIG. 4. Referring to FIG. 4, the pump 12 includes a controller 100, an electrically programmable read-only memory (EPROM) 102 having a built-in I/O interface 102a, a nonvolatile RAM 104, a real-time clock 106 and the display 92, all of which are interconnected by a communications bus 108. The display 92 has a backlight 110 which is selectively activated by an enable signal generated on a line 112 interconnecting the controller 100 and the backlight 110. Both the RAM 104 and the real-time clock 106 are connected to a battery 114 which supplies power to them only in the absence of system power. The controller 100 has a transmit buffer 116 and a receive buffer 118 connected to the communications bus 108.

The controller 100 controls the medicant infusion rate by periodically transmitting a control signal to an amplifier circuit 120 via a line 122 to drive a pump motor 124 which drives a pumping mechanism 126, such as a rotary pump wheel (not shown) adapted to make contact with a portion of the liquid conduit 16 (FIG. 1) connected to the catheter 14.

The controller 100 receives periodic inputs from a shaft encoder (SE) sensor 130, which is disposed on the shaft of the motor 124. The SE sensor 130 may be a two-phase motion sensing encoder which provides two signal outputs to the controller 100. The rotational speed of the motor 124 and its direction of rotation are determined by the controller 100 based upon the rate and phase relationship between the two signal outputs.

The SE encoder 130 periodically transmits the signals to the controller 100 via a line 132. Each time the signals are transmitted, an interrupt is generated, and the controller 100 compares the actual position of the motor shaft with its desired position, and transmits a new control signal, such as a pulse-width modulated signal, to the amplifier 120 via the line 122 to ensure that the actual speed of the motor 124 corresponds to the motor speed required for the desired medicant infusion rate. The interrupts caused by the SE sensor 130 are assigned to the highest priority so that they are responded to immediately, before any other actions are taken by the controller 100.

The pump 12 has a number of other features not described herein, which are disclosed in the following patent applications, each of which is incorporated herein by reference: U.S. Ser. No. 08/399,184, filed Mar. 6, 1995, entitled "Infusion Pump Having Power Saving Modes"; U.S. Ser. No. 08/398,977, filed Mar. 6, 1995, entitled "Infusion Pump With Selective Backlight"; U.S. Ser. No. 08/398,980, filed Mar. 6, 1995, entitled "Infusion Pump With Different Operating Modes"; U.S. Ser. No. 08/398,886, filed Mar. 6, 1995, entitled "Cassette For An Infusion Pump; U.S. Ser. No. 08/399,183, filed Mar. 6, 1995, entitled "Infusion Pump With Dual-Latching Mechanism"; U.S. Ser. No. 08/398,887, filed Mar. 6, 1995, entitled "Infusion Pump With Historical Data Recording."

Figure 5:
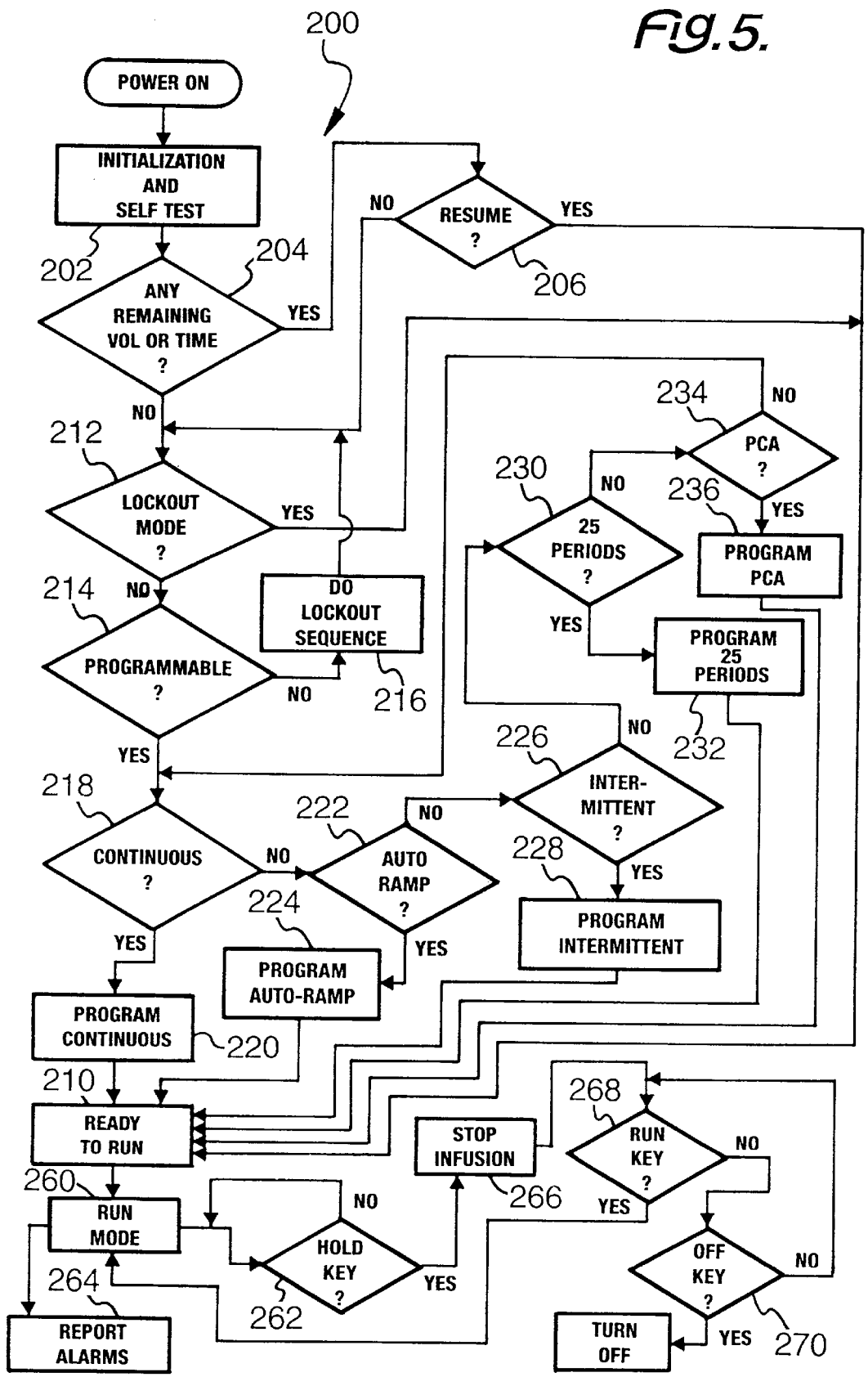
FIG. 5 is a flowchart of the overall operation of the infusion pump.

The operation of the infusion pump 12 is controlled by a computer program stored in the EPROM 102 and executed by the controller 100. A flowchart 200 of the overall operation is illustrated in FIG. 5. Referring to FIG. 5, when the pump 12 is turned on, at step 202 the pump is initialized and a test of the pump operation is performed. The pump 12 may be turned off temporarily during an infusion, in which case the pump 12 may continue the infusion when it is turned back on, as described below. At step 204, if there is any remaining volume of liquid to be infused by the pump or any additional time remaining for an infusion, which would be the case where the pump was temporarily turned off during an infusion, the program branches to step 206, where the user is asked, via a message displayed on the display 92, whether the previous infusion should be resumed. If the user answers yes (via the keypad 90), the program branches to a ready-to-run step 210. If the previous infusion is not to be resumed, the program branches to step 212.

The infusion pump 12 has a lockout mode in which the user may be prevented from programming the infusion parameters, such as the volume to be infused or the rate of infusion. For example, the pump 12 could be programmed by a medical assistant to deliver a particular infusion having a particular flow profile, flow rate and volume to be infused. After programming that infusion, the medical assistant could place the pump in lockout mode, which would prevent the patient from changing any of the infusion parameters. At step 212, if the pump 12 has been previously placed in lockout mode, the program branches directly to the ready-to-run step 210, bypassing all programming steps.

At step 212, if the pump is not in lockout mode, the program branches to step 214, at which point the program prompts the user, via the display 92, to input whether the patient should be allowed to program the pump during the subsequent infusion. If the pump is not to be programmable, the program branches to step 216 where a lockout sequence is performed by requesting the user to input which infusion modes should be locked out. If the pump is to be programmable by the patient, the program bypasses step 216.

The infusion pump 12 has five basic modes of infusion: 1) a continuous mode in which the pump delivers a single volume at a single rate; 2) an auto-ramp mode in which the pump delivers liquid at a rate that gradually increases to a threshold rate, stays constant at the threshold rate, and then gradually decreases; 3) an intermittent mode in which the pump delivers discrete liquid volumes spaced over relatively long periods of time, such as a liquid volume every three hours; 4) a custom mode in which the pump can be programmed to deliver a unique infusion rate during each of 25 different time periods; and 5) a pain-controlled analgesic (PCA) mode during which the pump will periodically infuse boluses of analgesic in response to periodic requests by the patient.

At step 218, the pump 12 generates on the display 92 the prompt "Continuous?" to the user. If the user desires to use the pump in its continuous mode, the user answers "yes" via the keypad 90, and the program branches to step 220 at which the continuous mode is programmed by the user by entering a number of infusion parameters, such as the desired infusion rate, the volume to be infused, etc. At step 218, if the user does not want to use the continuous mode, the user answers "No," and the program branches to step 222. Steps 222–236 are generally the same as steps 218 and 220, except that the user may be prompted for different infusion parameters, depending on which of the five possible infusion modes is selected.

After the completion of one of the steps 220, 224, 228, 232, or 236, the program branches to the ready-to-run step 210. When the user presses the "Run" key, the pump 12 enters the run mode 260 and infuses the patient with a liquid medicant in accordance with the infusion mode selected at one of steps 218, 222, 226, 230, 234 and the infusion parameters entered at one of steps 220, 224, 228, 232, 236. The pump 12 remains in the run mode 260 until the "Hold" key is pressed, as determined at step 262. Upon the occurrence of an alarm condition, an alarm is reported at step 264. At step 262, if the hold key is pressed, the infusion is stopped at step 266, and the pump 12 waits for the run key to be pressed at step 268 or the on/off switch to be turned off at step 270.

Summarizing the operation described above, if the pump is to be utilized in lockout mode, a medical assistant turns the pump on, programs the desired infusion mode at one of steps 220, 224, 228, 232, 236, and then turns the pump off. The programmed infusion parameters will be retained in the memory 104. The medical assistant would then turn the pump back on, press the "No" key in response to the "Programmable?" prompt at step 214, enter the lockout information at step 216, and then turn the pump off again. When the patient subsequently turned on the pump to perform the infusion, the program would proceed from step 212 directly to the ready-to-run step 210, which would prevent the patient from altering the infusion parameters.

If the lockout mode was not utilized, the medical assistant or the patient could turn the pump on, program the desired infusion mode, and then press the "Run" key to start the infusion without ever turning the pump off.

During programming and operation, the infusion pump 12 automatically records in the non-volatile memory 104 all significant infusion data to generate a complete historical data record which can be later retrieved from the memory 104 and used for various purposes, including clinical purposes to aid in determining how effective a particular infusion therapy was and treatment purposes to confirm that the prescribed infusion was actually delivered.

Figure 6:
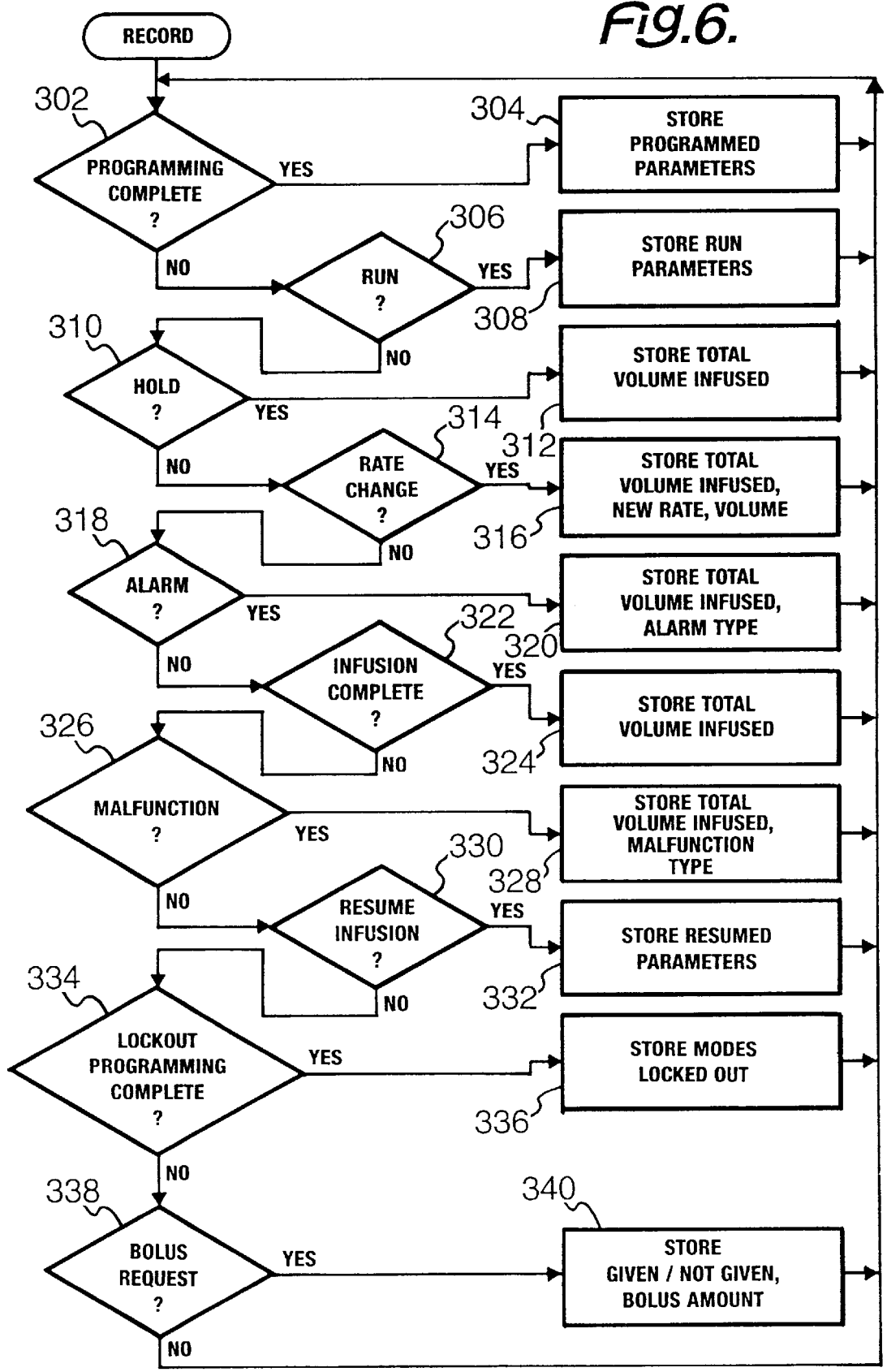
FIG. 6 illustrates a number of data-recording steps performed during the operation of the infusion pump.

FIG. 6 illustrates various steps at which infusion data is recorded that are performed during the overall pump operation shown generally in FIG. 5. The infusion data recorded in the memory 104 is set forth in Table 1 below. A number of events which trigger the storage of data are listed in the left-hand column of Table 1, and the infusion data that is recorded upon the occurrence of each event is listed in the right-hand column of Table 1. The time at which the infusion data is recorded, which is determined by the real-time clock 106, is also stored along with the infusion data.

TABLE 1

| EVENT | DATA RECORDED |
| --- | --- |
| Power On | Date and Time |
| Program | Infusion parameters. See TABLE 2. |
| Run | Infusion parameters. See TABLE 2. |
| Hold | Total Volume Infused |
| Restart | Time of Restart |
| Rate Changes | Total Volume Infused, Rate, Volume |
| Alarms | Total Volume Infused, Alarm Type |
| Infusion Complete | Total Volume Infused |
| Malfunctions | Total Volume Infused, Malfunction Type |
| Resume | Infusion parameters. See TABLE 2. |
| Maintenance Date | Date |
| Patient ID | Patient ID Number |
| Serial No. | Serial Number |
| Language Change | New Language |
| Lockout | Modes Locked Out |
| Pressure Select | New Pressure Setting |
| Bolus Request | Given/Not Given, Bolus Amount |
| Titration | New Parameters |
| Power Off | Time of Power Off |
| Version No. | Software Version Number |

Referring to Table 1 and FIG. 6, when the power to the infusion pump 12 is turned on, the date and time of the power turn-on is recorded. When the pump is completely programmed pursuant to one of steps 220, 224, 228, 232, 236 (FIG. 5) as determined at step 302, the programmed infusion parameters are stored at step 304, along with the time of such storage. The particular parameters that are stored depend upon which infusion mode was programmed. Several examples of infusion parameters that are stored for each of a number of infusion modes are illustrated in Table 2 set forth below.

TABLE 2

| INFUSION MODE | INFUSION PARAMETERS |
| --- | --- |
| Continuous | Infusion Mode |
|  | Infusion Rate |
|  | Volume To Be Infused |
|  | Delay Time |
|  | Total Bag Volume |
|  | KVO Rate |
| Auto-Ramp | Infusion Mode |
|  | Infusion Rate |
|  | Volume To Be Infused |
|  | Delay Time |
|  | Total Bag Volume |
|  | Duration of Up-Ramp |
|  | Duration of Down-Ramp |
|  | KVO Rate |
| Intermittent | Infusion Mode |
|  | Total Infusion Time |
|  | Number of Doses |
|  | Dose Time |
|  | Dose Volume |
|  | KVO Rate |

When the pump enters the run mode 260 (FIG. 5) as determined at step 306, the time at which the run mode was begun, along with the parameters pursuant to which the infusion is performed, are stored at step 308.

At step 310, if the hold key is pressed, then the time at which the hold key was pressed along with the total volume infused at the time the hold key was pressed are stored at step 312. The pump also stores any infusion rate changes, such as changes caused by switching from a continuous rate to a keep-vein-open (KVO) rate, or in the intermittent mode, changing from a KVO rate to a higher infusion rate, the presence of which are detected at step 314. The new rate and the time at which the new rate started are stored at step 316.

At step 318, if any alarms are generated, the alarm type, the time at which the alarm occurred, and the total volume infused at the time of the alarm are recorded at step 320. If the infusion is completed as determined at step 322, the program branches to step 324 where the time at which the infusion was completed is stored along with the total volume infused. At step 326, if there is a malfunction, the malfunction type, the time at which the malfunction occurred, and the total volume infused at the time of the malfunction are recorded at step 328.

At step 330, if the infusion is resumed (when the pump is turned back on after having been turned off during an infusion), the time at which the infusion is resumed along with the infusion parameters are stored at step 332. Upon the completion of the programming of a lockout sequence as determined at step 334 (i.e. after step 216 of FIG. 5), the time at which the programming of the lockout was completed is stored along with the infusion modes that were locked out. At step 338, upon the detection of a bolus request, the time at which the bolus was requested is stored at step 340, along with an indication whether the bolus was actually given and the amount of the bolus.

Figure 6A:
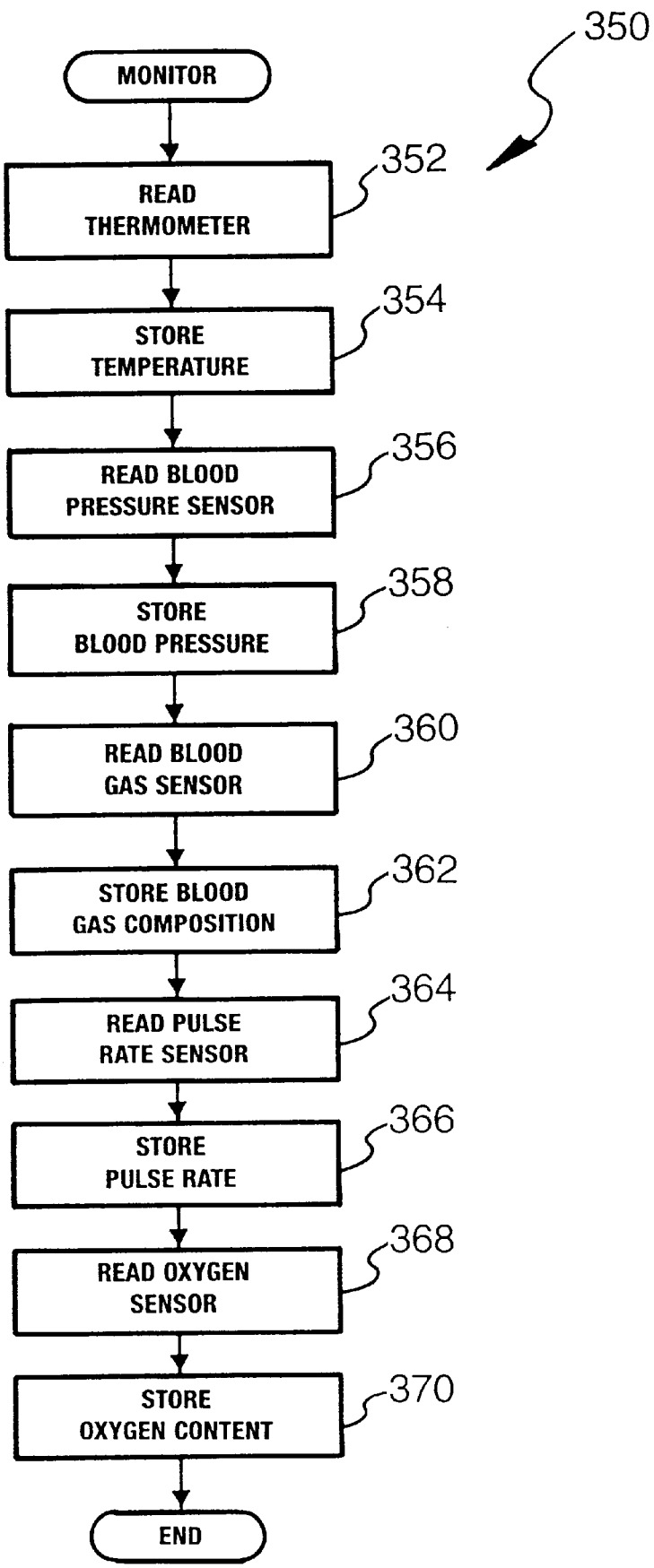
FIG. 6A is a flowchart of a routine for storing patient condition data generated by the sensors of FIG. 1.

FIG. 6A is a flowchart of a routine 350 for periodically storing patient medical condition data generated by the sensors 40, 44, 48, 52, 56 of FIG. 1 in the nonvolatile RAM 104. Referring to FIG. 6A, at step 352 the thermometer 40 is read, and at step 354 data generated by the thermometer 40 is stored in the RAM 104. At step 356 the blood pressure sensor 44 is read, and at step 358 data generated by the sensor 44 is stored in the RAM 104. At step 360 the blood gas sensor 48 is read, and at step 362 data generated by the sensor 48 is stored in the RAM 104. At step 364 the pulse rate sensor 52 is read, and at step 366 data generated by the sensor 52 is stored in the RAM 104. At step 368 the blood oxygen sensor 56 is read, and at step 370 data generated by the sensor 56 is stored in the RAM 104. The routine 350 may be performed periodically, such as every minute for example. Other ways of reading the sensors could be utilized, and the particular manner in which the sensors are read is not considered important to the invention.

Figure 7:
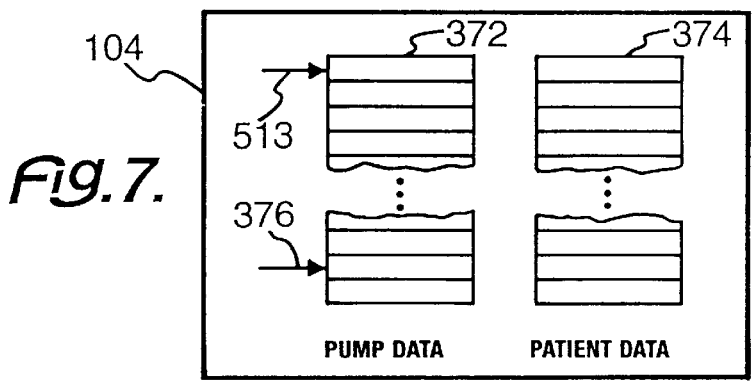
FIG. 7 is a representation of a portion of the memory of the infusion pump.

FIG. 7 illustrates the data organization of a portion of the RAM 104 in which infusion data (the data stored during the steps of FIG. 6) and patient medical condition data (the data stored during the steps of FIG. 6A) are stored. Referring to FIG. 7, the infusion data is stored in a number of memory locations 372, and the medical condition data is stored in a number of memory locations 374. Data may be written to the memory locations 372 utilizing a pointer 376 which specifies the memory location at which data should be next stored.

Figure 8:
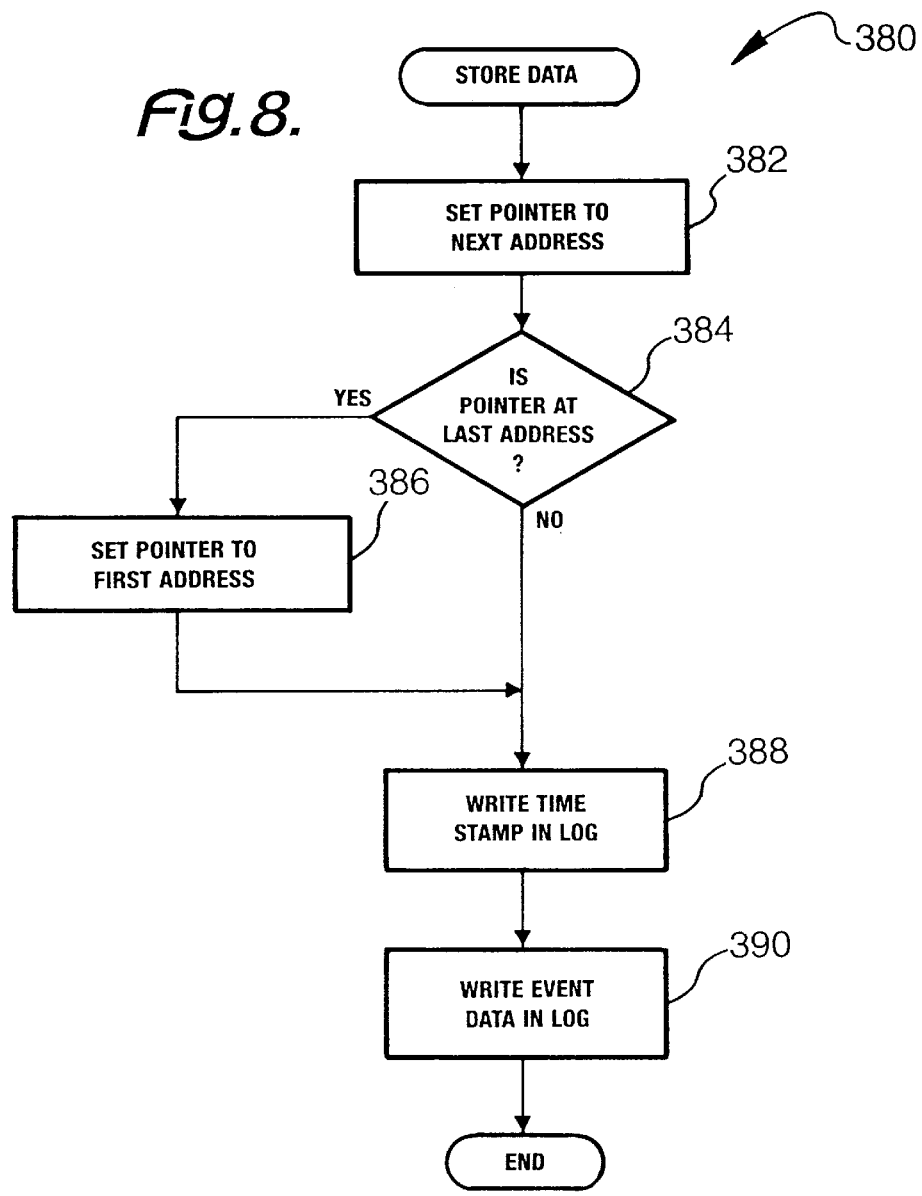
FIG. 8 is a flowchart of a store data routine which can be used to store data relating to the operation of the infusion pump and data relating to the condition of a patient.

FIG. 8 is a flowchart of a routine 380 for storing data in the memory locations 372, 374. Referring to FIG. 8, at step 382 the pointer 376 is set to the address of the next memory location 372 in which data is to be stored. At step 384, if the pointer 376 is at the last memory location in which data may be stored, the routine branches to step 386 where the pointer is set to the address of the first memory location in which data may be stored. As a consequence of steps 384, 386, the contents of the memory locations 372 are periodically overwritten with new data; however, the number of memory locations 372 is sufficiently large so that several months of data, for example, is stored before being overwritten. At steps 388 and 390 the data is stored in the memory location 372 specified by the pointer 376 (the data includes a time stamp generated from the real-time clock 106 and event data specifying the particular infusion event). Data may be stored in the memory locations 374 in the same manner.

Figure 9:
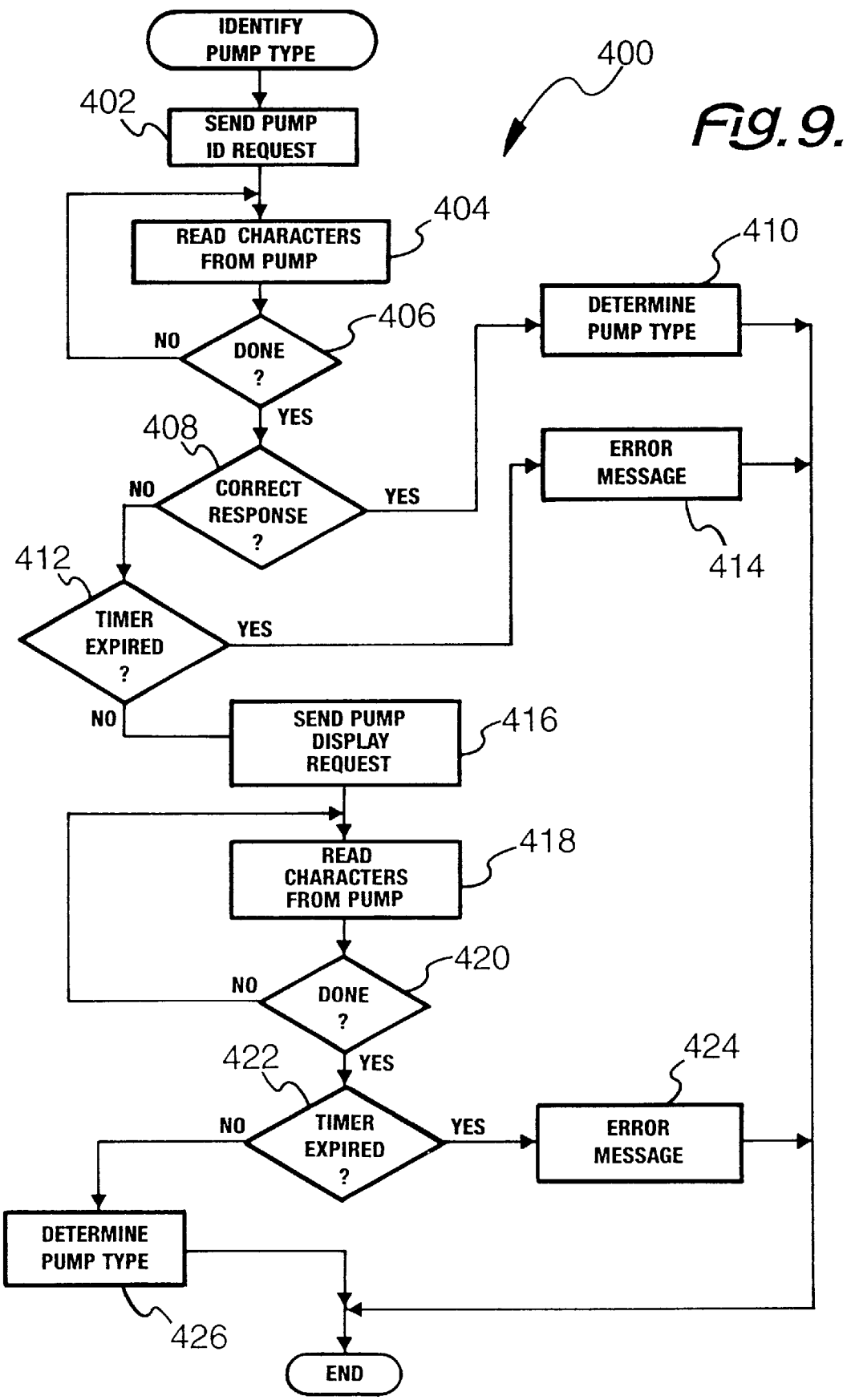
FIG. 9 is a flowchart of a routine which may be used to identify the type of infusion pump to which the remote monitor/controller is coupled.
Figure 10:
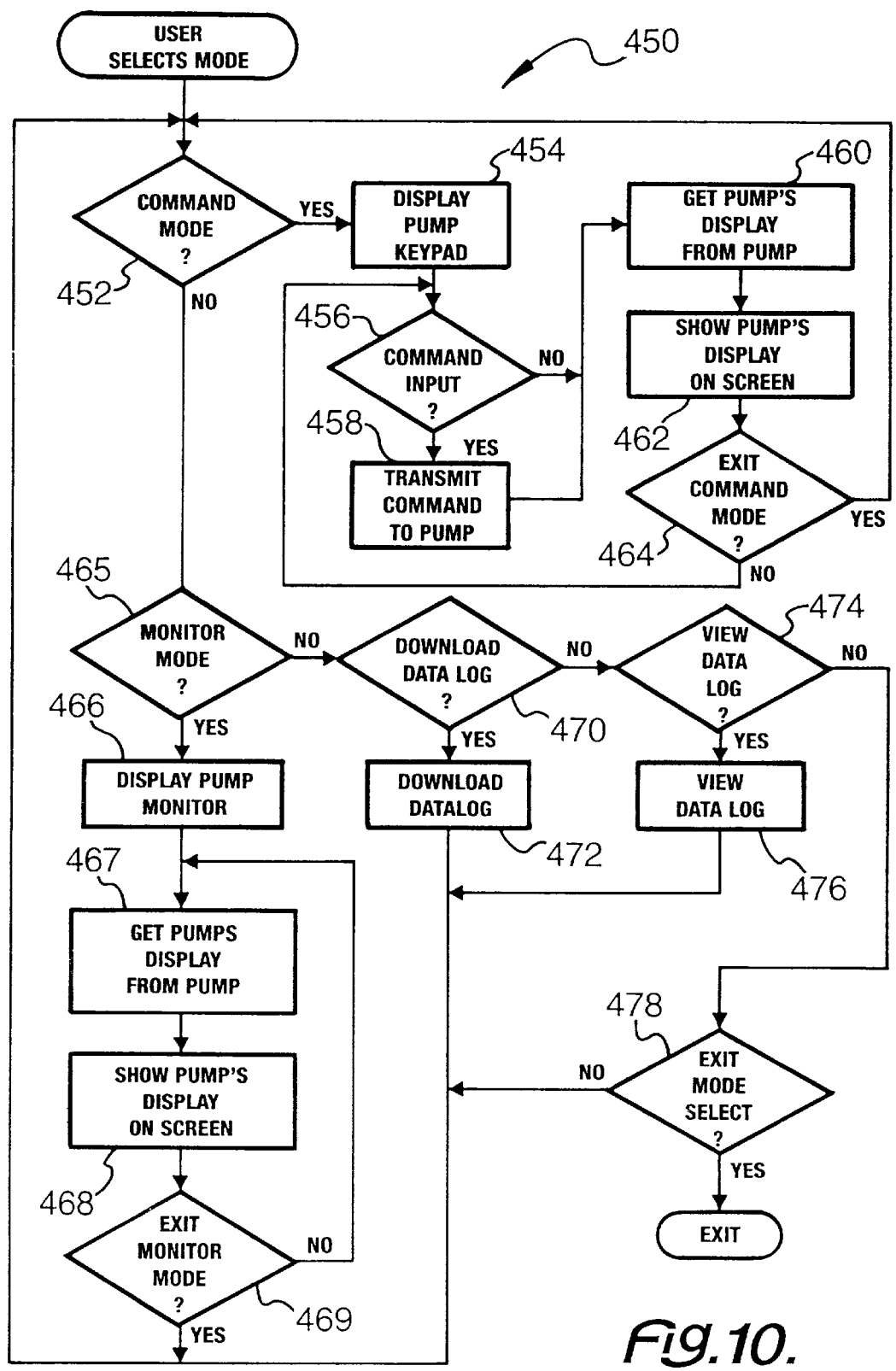
FIG. 10 is a flowchart of a main operating routine of the remote monitor/controller.
Figure 12:
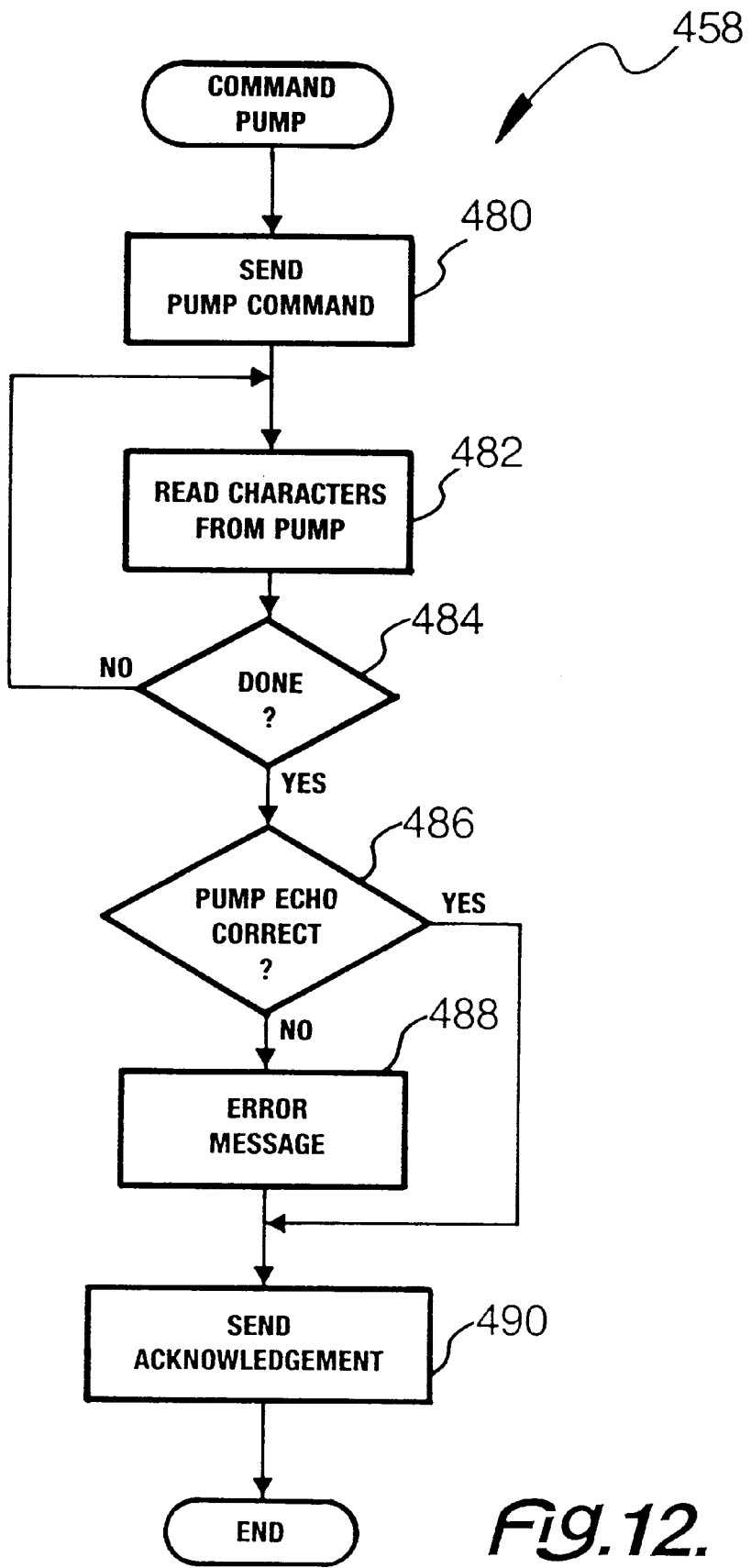
FIG. 12 is a flowchart of a command pump routine that is performed by the remote monitor/controller.

FIGS. 9, 10, and 12 are flowcharts of various routines that are performed by the remote monitor/controller 20. As described in more detail below, the remote monitor/ controller 20 may be used to monitor the operation of the infusion pump 12, to control the operation of the infusion pump 12, and/or to transfer infusion data and patient data from the infusion pump 12 so that such data can be reviewed by a health care professional at a location remote from the patient.

The remote monitor/controller 20 is designed to interface with different types of infusion pumps. In order to determine which type of infusion pump the remote monitor/controller 20 is operatively coupled, a pump identification routine 400 performed after the communication link between the remote monitor/controller 20 and the infusion pump 12 is established. Referring to FIG. 9, at step 402 the remote monitor/ controller 20 transmits a pump identification (ID) request to the infusion pump 12 via the communication link 38. In response to the pump ID request, the pump 12 transmits a multi-character ID code back to the remote monitor/ controller 20. The ID code may include, for example, one or more characters identifying the pump model and/or one or more characters identifying the software version of the pump. At step 404, the remote monitor/controller 20 reads the characters sent from the pump 12 until all characters are received as determined at step 406 or until a predetermined time period, e.g. five seconds, elapses. The time period may be determined by a timer (not shown). The remote monitor/ controller 20 may determine that all characters have been received by, for example, identifying one or more termination characters, such as a carriage-return character <CR> followed by a line-feed character <LF>.

Step 408 determines whether a correct response was received from the pump 12, which may be determined checking the characters received from the pump 12 against a list of possible ID codes. If a correct response was received, the routine branches to step 410 where the pump type is determined, for example, by comparing the received pump ID code with at least one possible ID code which identifies a particular type of infusion pump, or by comparing the received pump ID code with a number of possible ID codes, each of which identifies a particular type of infusion pump. As used herein, the "type" of infusion pump may relate to the model of the pump or the software version of the pump.

If a correct response was not received as determined by step 408, at step 412 the routine determines whether the predetermined time period measured by the timer has expired prior to receiving a termination character. If so, the routine branches to step 414 where an error message is generated due to the pump's failure to respond to the pump ID request.

At step 412, if some type of response (not a correct response) was received before the timer expired, the routine branches to step 416. Steps 416–426 comprise a second way of determining the type of infusion pump 12 connected to the remote monitor/controller 20, which is based on the number of characters in the display 92 of the pump 12. For example, a first type of infusion pump may have a display capable of displaying 12 characters, whereas a second type of infusion pump may have a display capable of displaying 32 characters. Steps 416–426 determine the type of infusion pump based on the number of characters in the display.

At step 416, the remote monitor/controller 20 transmits a pump display request to the infusion pump 12 to request the pump 12 to transmit the content of its display 92. At step 418, the remote monitor/controller 20 reads the display characters transmitted from the pump 12. At step 420, if a predetermined period of time has elapsed or if a terminating character is received, the routine branches to step 422. At step 422, if the predetermined time period measured by the timer elapsed prior to the receipt of a terminating character, the routine branches to step 424 where an appropriate error message is generated. At step 426, the type of pump is determined based on the number of display characters that were received.

The routine could also exit step 420 if a predetermined number of characters are received. In that case, where the remote monitor/controller 20 was designed to interface with two different types of infusion pumps, one having a display capability of 12 characters and another having a display capability of 32 characters, if the remote monitor/controller 20 received more than 12 display characters at step 420, it would immediately be able to determine that the pump type corresponded to a pump with a 32-character display capability.

The remote monitor/controller 20 allows four basic functions to be performed, including controlling the infusion pump 12, monitoring the operation of the pump 12, transferring infusion data and patient medical condition data from the pump 12 to the remote monitor/controller 20, and viewing the data. The user may perform one of those functions by selecting an operational mode displayed on the display device 78 (FIG. 2) of the remote monitor/controller 20 via the mouse 82. These modes include a command mode in which a health care professional at the remote monitor/ controller 20 may transmit command signals to the infusion pump 12 to control its operation, a monitoring mode in which the infusion pump 12 will continually transmit the contents of its visual display 92 to the remote monitor/ controller 20, a download data mode in which infusion data and/or patient medical condition data is transferred from the pump 12 to the remote monitor/controller 20, and a view data mode in which the infusion data and patient data may be viewed on the display 78 of the remote monitor/controller 20.

FIG. 10 illustrates a flowchart 450 of the basic operation of the remote monitor/controller 20. Referring to FIG. 10, at step 452, if the user selected the command mode described above, the routine branches to step 454 where a display of the keypad 90 of the infusion pump 12 is shown on the display device 78. The display shown at step 454 comprises a plurality of virtual entry keys having a spatial configuration substantially the same as the entry keys of the keypad 90 of the particular infusion pump type which is connected to the remote monitor/controller 20. An example of such a visual display is shown in FIG. 11A.

Figure 11A:
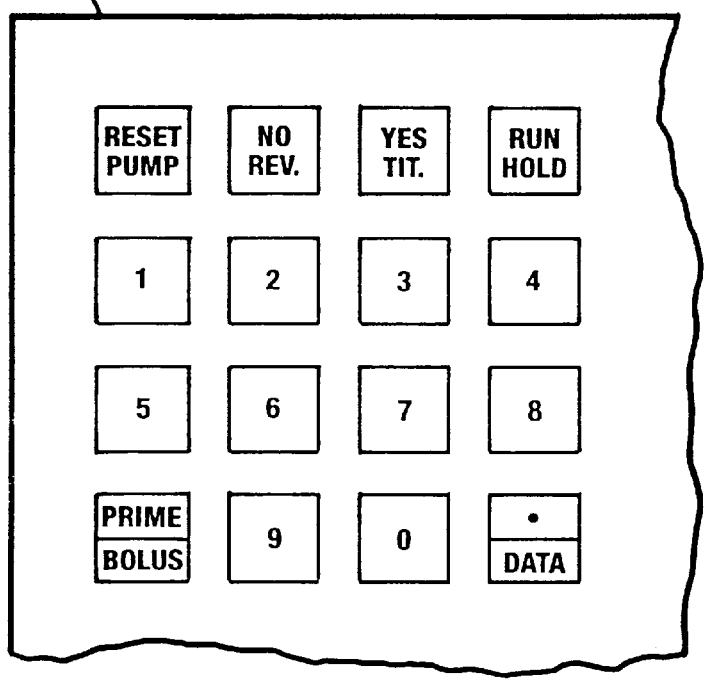
FIGS. 11A–11B illustrate portions of visual displays generated by the remote monitor/controller.
Figure 11B:
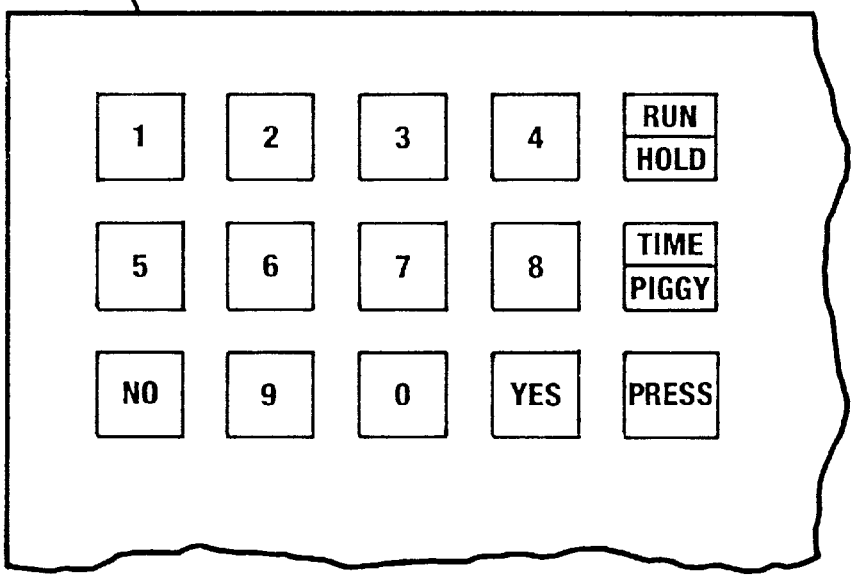

It should be noted that the virtual keypad shown in FIG. 11A is the same as the actual keypad 90 of the pump 12, which is shown in FIG. 3 (except that the on/off key of the pump 12 is replaced with a reset key in the virtual key display). Where a different type of pump having a different keypad is attached to the remote monitor/controller 20, that particular keypad is displayed on the display device 78. An example of a different virtual keypad is shown in FIG. 11B. Various virtual keypad configurations may be stored in the memory of the remote monitor/controller 20, each virtual keypad configuration having a pump type code associated therewith. Since the remote monitor/controller 20 initially determined the type of pump to which it was attached (via the routine of FIG. 9), it can retrieve from memory and display the corresponding virtual keypad for that type of pump.

After the virtual keypad is displayed, the health care professional may control the operation of the infusion pump 12 by selecting any of the virtual keys with the mouse 82. Other ways of selecting the keys could be utilized, such as a touch-sensitive screen or a display screen activated by radiation sensors. The infusion pump 12 responds to commands entered via its keypad 90 and to commands generated from the remote monitor/controller 20. At steps 456 and 458, any commands entered by the health care professional are transmitted to the infusion pump 12, and at steps 460 and 462, the display of the pump 12 is transferred to the remote monitor/controller 20 and displayed on the display device 78 of the remote monitor/controller 20. At step 464, if the user exits the command mode, the routine branches back to step 452.

At step 465, if the health care professional selected the monitor mode, the routine branches to step 466 where a visual display of the pump display 92 is shown on the display device 78. At step 467, the contents of the pump display 92 are transferred to the remote monitor/controller 20, and at step 468 those contents are displayed in the visual display generated at step 466. At step 469, if the user exits the monitor mode, the routine branches back to step 452; otherwise, the routine branches back to step 467 so that the contents of the pump display 92 are continuously shown on the display device 78 at step 468 (the display 92 of the infusion pump 12 changes in accordance with the pump operation so that the pump operation can be monitored by viewing the display 92). Step 467 may be accomplished, for example, by transmitting a pump display request to the pump 12 (via steps similar to steps 416–420 described above).

If the health care professional inputs a request to download data from the pump 12 to the remote monitor/controller 20 as determined at step 470, the routine branches to step 472 where the data transfer is accomplished, as described below in connection with FIGS. 13–14. If the user inputs a view data log request as determined at step 474, the routine branches to step 476 where data previously downloaded at step 472 can be viewed on the display device 78 of the remote monitor/controller 20. The user may exit the mode select routine 450 via step 478.

FIG. 12 illustrates one routine that could be used to implement the transmit command step 458 shown schematically in FIG. 10. Referring to FIG. 12, the pump command is transmitted from the remote monitor/controller 20 at step 480, and then the infusion pump 12 transmits to the remote monitor/controller 20 an echo of the command so that the remote monitor/controller 20 knows that command was received properly by the pump 21. The characters making up the echo are received at steps 482–484, and if the echo is not correct, an error message is displayed to the health care professional. At step 490, the remote monitor/controller 20 sends an acknowledgement of the echo to the pump 12.

The transfer of data from the infusion pump 12 to the remote monitor/controller 20 shown schematically in step 468 of FIG. 10 is accomplished via a receive interrupt service routine 500 and a transmit interrupt service routine 550 that are performed by the infusion pump 12. Flowcharts of the routines 500, 550 are shown in FIGS. 13 and 14.

Figure 13:
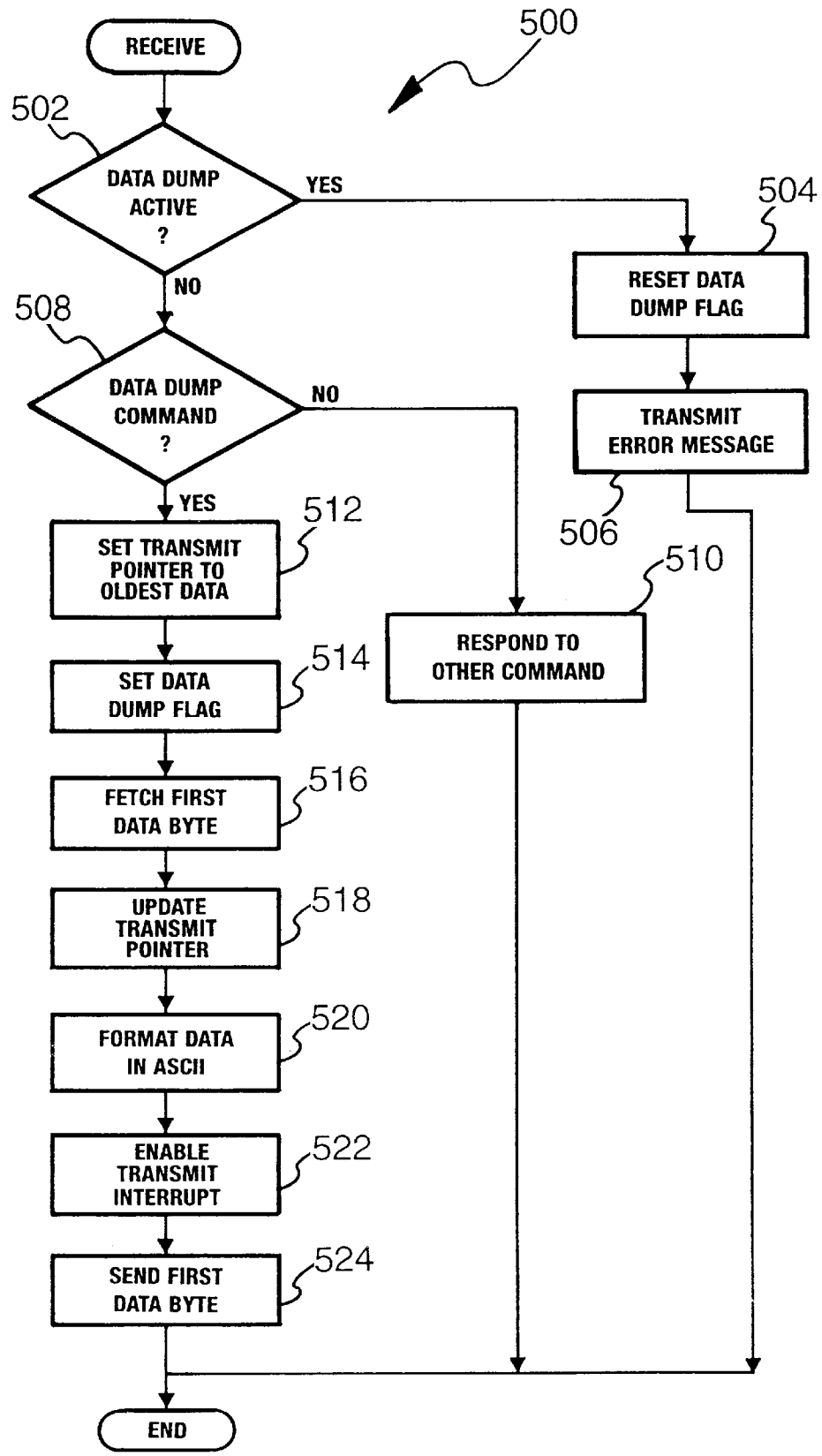
FIG. 13 is a flowchart of a receive routine that is performed by the infusion pump.
Figure 14:
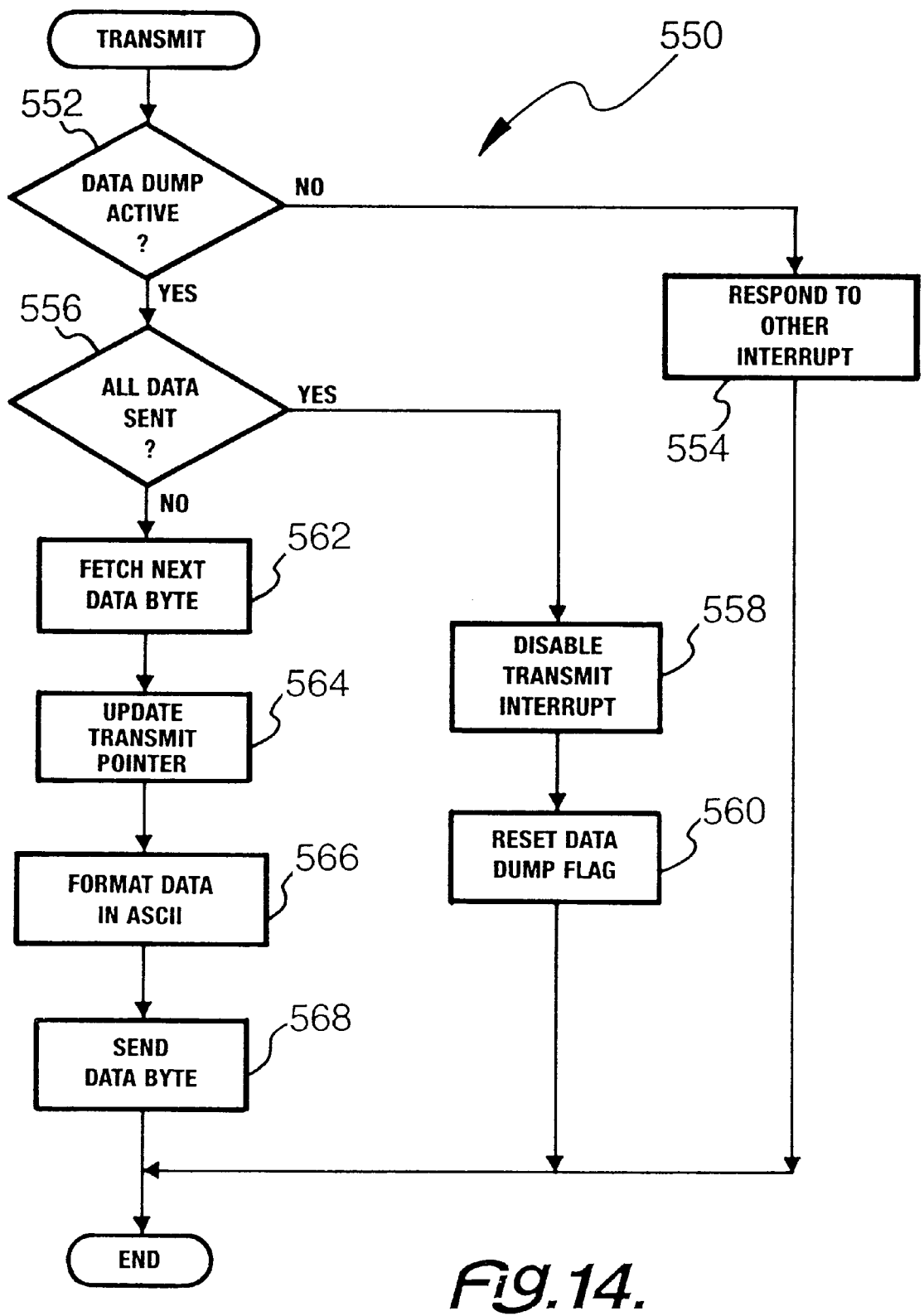
FIG. 14 is a flowchart of a transmit routine that is performed by the infusion pump.

The receive routine 500 shown in FIG. 13 is invoked upon the generation of a receive interrupt by the pump controller 100. The receive interrupt indicates that a message has been received in the receive buffer 118 of the controller 100 from the remote monitor/controller 20. When a download data command is sent to the infusion pump 12 (as determined at step 466 of FIG. 10), a data dump flag is set to logic "1," indicating that a data transfer or dump from the pump 12 to the remote monitor/controller 20 is in progress. The data transfer is performed in a segmented fashion. Instead of sending all of the infusion data and patient data stored in the RAM 104 to the remote monitor/controller 20 in a single, continuous stream, the data is sent in segmented portions, each of which is separated in time from its adjacent portions by a period of time, e.g. 100 microseconds.

Referring to FIG. 13, when the routine begins at step 502, a character or message will have been just received in the receive buffer 118. At step 502, if the data dump flag is active, meaning that a data transfer is already in progress, then the routine branches to step 504, where the data dump flag is set to logic "0," effectively terminating the data dump operation, and an error message is transmitted to the remote monitor/controller 20 at step 506. This is done to prevent the data dump operation from interfering with any commands that are transmitted from the remote monitor/controller 20 to the infusion pump 12.

If the data dump flag was not active as determined at step 502, the routine branches to step 508 where the message just received in the receive buffer 118 is checked to determine whether it is a data dump command. If it is not, then the routine branches to step 510 where the pump 12 responds to the command.

If the message is a data dump command, the routine branches to step 512 where a transmit pointer 513 (see FIG. 7) is set to the oldest data in the RAM 104 that has not yet been transmitted to the remote monitor/controller 20. At step 514, the data dump flag is set to logic "1" since a new data transfer operation is beginning. At step 516, the data byte specified by the transmit pointer 513 is retrieved from the RAM 104, and at step 518 the position of the transmit pointer 513 is updated (e.g. incremented) to point to the address of the next data byte to be transmitted. At step 520, the data byte retrieved at step 516 is formatted in ASCII; at step 522 the transmit interrupt is enabled; and at step 524 the reformatted data byte is transmitted from the infusion pump transmit buffer 116 to the remote monitor/controller 20 over the data link 38.

When the first data byte is sent out from the transmit buffer 116, a transmit interrupt is generated by the controller 100 to indicate that the transmit buffer 116 is empty and that another data byte can be transmitted. Upon the generation of the transmit interrupt, the transmit routine 550 is performed. Referring to FIG. 14, at step 552 the status of the data dump flag is checked. If the flag is not active, meaning that a data dump operation is not in progress, the routine branches to step 554 where the routine responds to the other interrupt. If the data dump flag is active, then the routine branches to step 556, where it determines whether all of the segmented portions of the infusion data and/or patient data have been transmitted. This may be accomplished, for example, by determining if the transmit pointer 513 and the pointer 376 (FIG. 7) are pointing to the same memory location. If all the requested data has been sent, the routine branches to step 558, where the transmit interrupt is disabled, and then to step 560 where the data dump flag is reset to logic "0," effectively ending the data transfer operation.

If not all the data has been transferred as determined at step 556, the routine branches to step 562 where the data byte specified by the transmit pointer 513 is retrieved from the RAM 104. At step 564 the position of the transmit pointer is updated to point to the address of the next data byte to be transmitted. At step 566, the data byte retrieved at step 562 is formatted in ASCII, and at step 568 the reformatted data byte is transmitted from the infusion pump transmit buffer 116 to the remote monitor/controller 20 over the data link 38.

The transmit interrupts generated by the controller 100 to transfer the segmented data portions to the remote monitor/controller 20 are assigned a lower priority than the interrupts generated in response to input of the shaft encoder sensor 130, which is necessary to provide the desired infusion rate. Consequently, the transfer of the infusion data and patient data does not interfere with the ability of the pump 12 to provide the desired infusion rate, and the data transfer can occur while the pump is infusing the patient with the medicant.

FIG. 15 is an illustration of a graphical user menu that may be shown on the display device 78 of the remote monitor/controller 20. The health care professional may select particular data for transfer or viewing, via a number of different parameters such as beginning date, ending date, types of data, etc. The particular manner in which particular data may be selected for transfer or viewing is not considered important to the invention.

The ability to generate patient medical condition data via the sensors 40, 44, 48, 52, 56 and transfer that data to the remote monitor/controller allows a health care professional to review and analyze the patient medical condition data and alter the infusion therapy applied to the patient by the infusion pump 12 based upon such review and analysis. Alternatively, instead of such manual analysis by a health care professional, an automatic means for analyzing the patient medical condition data and altering the infusion therapy could be provided.

Modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. A medical apparatus, comprising:
   a programmable medical device disposed at a first room location;
   a sensor for detecting a medical condition of a patient, the sensor being disposed at the first room location, being connected to the patient and being connected to the programmable medical device;
   wherein the programmable medical device comprises a memory storing medical condition data relating to the medical condition of the patient detected by said sensor; and
   a remote controller for controlling the programmable medical device, the remote controller being disposed at a second room location remote from the first room location at which the programmable medical device is disposed, the remote controller comprising:
   a controller for controlling the programmable medical device; and
   a remote monitor operatively coupled to the sensor via said programmable medical device effective for retrieving stored medical condition data from the memory for monitoring the stored medical condition detected by the sensor.

2. The medical apparatus according to claim 1 wherein the sensor comprises at least one of a blood pressure sensor, a blood gas sensor, a pulse rate sensor and a blood-oxygen sensor.

3. The medical apparatus of claim 1 further comprising a routine for transmitting said stored medical condition data detected by said sensor, responsive to a data dump command.

4. An apparatus as defined in claim 1 further comprising a routine for transmitting medical condition data relating to said medical condition of the patient detected by the sensor from the first room location to the remote monitor at said second location.

5. An apparatus as defined in claim 1 wherein the programmable device comprises an infusion pump for infusing a drug into the patient.

6. An apparatus as defined in claim 1 wherein the programmable medical device comprises:
   a liquid injection device adapted to be connected to the patient;
   a conduit connected to the liquid injection device;
   a pumping mechanism for pumping a liquid drug through the conduit and into the patient via the liquid injection device; and
   a controller for controlling the pumping mechanism.

7. An apparatus as defined in claim 1 wherein the sensor generates an output signal representative of the condition of the patient and wherein the output signal is input to the programmable medical device.

8. A medical apparatus, comprising:
   programmable medical treatment device for automatically administering a medical treatment directly to a patient, the programmable medical treatment device being disposed at a first room location, the programmable medical treatment device comprising:
   a liquid injection device adapted to be connected to the patient;
   a conduit connected to the liquid injection device;
   a pumping mechanism for pumping a liquid drug through the conduit and into the patient via the liquid injection device; and
   a controller for controlling the pumping mechanism;
   a sensor for detecting a medical condition of the patient, the sensor being disposed at the first room location and being connected to the patient and to the programmable treatment device;
   wherein the programmable medical treatment device further comprises a memory storing medical condition data relating to the medical condition of the patient detected by the sensor;
   a remote controller for controlling the programmable medical treatment device, the remote controller being disposed at a second room location remote from the first room location at which the programmable medical treatment device is disposed, the remote controller comprising
   a controller for controlling the programmable medical treatment device; and
   a remote monitor operatively coupled to the sensor via the programmable medical treatment device effective for retrieving the stored medical condition data from the memory for monitoring the medical condition detected by the sensor; and
   apparatus for transmitting the stored medical condition data relating to the medical condition of the patient detected by the sensor from the first room location to the remote monitor.

9. A medical apparatus according to claim 8 wherein the sensor comprises at least one of a blood pressure sensor, a blood gas sensor, a pulse rate sensor and a blood-oxygen sensor.

10. An apparatus as defined in claim 8 wherein the remote monitor comprises a display for displaying the medical condition data.

11. An apparatus as defined in claim 8 wherein the sensor generates an output signal representative of the condition of the patient and wherein the output signal is input to the programmable medical treatment device.

12. A medical apparatus comprising:
- a medical treatment device for administering a medical treatment directly to a patient at a patient site, the medical treatment device being disposed at the patient site;
- a sensor disposed at the patient site for detecting a medical condition of the patient, the sensor being connected to the patient and to the medical treatment device;
- wherein the medical treatment device includes a memory storing medical condition data relating to the medical condition of the patient detected by the sensor;
- a remote controller at a second location remote from the patient site for controlling the medical treatment device, the remote controller comprising a device for controlling the medical treatment device to change the medical treatment administered to the patient; and
- a remote monitor disposed at the second location operatively coupled to the sensor via a telephone link and the medical treatment device effective for retrieving the stored medical condition data from the memory for monitoring the medical condition detected by the sensor.

13. The medical apparatus of claim 12 further comprising apparatus for enabling bi-directional voice data communication over the telephone line between the medical treatment device and the remote controller.

14. The medical apparatus according to claim 12 wherein the sensor comprises at least one of a blood pressure sensor, a blood gas sensor, a pulse rate sensor and a blood-oxygen sensor.

15. The medical apparatus as defined in claim 12 wherein the medical treatment device comprises a programmable infusion pump for infusing a drug into the patient.

* * * * *